United States Patent
Shelton et al.

(10) Patent No.: US 9,488,447 B2
(45) Date of Patent: Nov. 8, 2016

(54) PERSONAL COOLING DEVICE FOR USE WITH BODY ARMOR

(71) Applicants: Billy A. Shelton, Donna, TX (US); Billy R. Shelton, Donna, TX (US)

(72) Inventors: Billy A. Shelton, Donna, TX (US); Billy R. Shelton, Donna, TX (US)

(*) Notice: Subject to any disclaimer, the term of this patent is extended or adjusted under 35 U.S.C. 154(b) by 522 days.

(21) Appl. No.: 14/026,817

(22) Filed: Sep. 13, 2013

(65) Prior Publication Data

US 2014/0069617 A1    Mar. 13, 2014

Related U.S. Application Data

(60) Provisional application No. 61/700,497, filed on Sep. 13, 2012.

(51) Int. Cl.
| | |
|---|---|
| *A61F 7/00* | (2006.01) |
| *F41H 1/02* | (2006.01) |
| *A41D 13/002* | (2006.01) |

(52) U.S. Cl.
CPC ............ *F41H 1/02* (2013.01); *A41D 13/0025* (2013.01); *A61F 7/00* (2013.01); *A61F 2007/0064* (2013.01)

(58) Field of Classification Search
USPC .................................................. 607/96–114
See application file for complete search history.

(56) References Cited

U.S. PATENT DOCUMENTS

| | | | | |
|---|---|---|---|---|
| 3,468,299 A | * | 9/1969 | Amato | ............... A41D 13/0025 126/204 |
| 2012/0203311 A1 | * | 8/2012 | Clemente | .................. A61F 7/00 607/96 |

* cited by examiner

Primary Examiner — Joseph Stoklosa
Assistant Examiner — Adam Avigan
(74) Attorney, Agent, or Firm — Gunn, Lee & Cave, P.C.

(57) ABSTRACT

A personal cooling device with a network of tubular members, each tubular member having an inner surface defining a flowpath, an outer surface, and at least two channels extending between the flowpath and the outer surface. The network has an inlet. The at least two channels of each tubular member have differently-sized volumes, with the channels having the larger volumes closer to the network inlet than the channels having the smaller volumes. The device also includes a pump having an inlet and an outlet, and a length of connection tubing in fluid communication with the outlet of the pump and the inlet of the network of tubular members.

3 Claims, 2 Drawing Sheets

PERSONAL COOLING DEVICE FOR USE WITH BODY ARMOR

CROSS-REFERENCES TO RELATED APPLICATIONS

This original nonprovisional application claims priority to and the benefit of U.S. provisional application Ser. No. 61/700,497, filed Sep. 13, 2012, and which is incorporated by reference herein.

STATEMENT REGARDING FEDERALLY SPONSORED RESEARCH OR DEVELOPMENT

Not applicable.

BACKGROUND OF THE INVENTION

1. Field of the Invention

The present invention relates to personal cooling devices. More specifically, the device relates to personal cooling devices used in conjunction with body armor, such as bulletproof vests.

2. Description of the Related Art

Body armor is an essential piece of equipment to law enforcement officers. Studies have shown that forty-two percent of officer deaths might have been prevented if the officer had been wearing body armor. From 1973 to 2000, 2500 saved lives of law enforcement personnel were attributed to the use of body armor. According to FBI research, the risk of a fatal ballistic injury to officers who do not routinely wear body armor is fourteen times greater than for those who do.

But body armor, by its nature, is encumbering and uncomfortable. In environments particularly susceptible to warmer weather, such as the arid regions of the southwest United States, temperatures during the summer months easily reach ninety degrees Fahrenheit, making those who must wear body armor, such as bulletproof vests, as part of their job, particularly susceptible to heat stroke and dehydration. Under normal conditions, the ballistic panel or the armor insulates the wearer and causes excess heat to be retained, while waterproof vests prevent effective cooling. The problem only exacerbates in the event the vest wearer must exert effort through the performance of duties.

In fact, one common mistake in the law enforcement arena is choosing the highest level of protection at the expense of comfort. Officers outfitted with uncomfortable armor have a tendency to leave the equipment at home rather than routinely wear it.

A number of solutions exists that attempt to address the problem of cooling the wearer of body armor. For example, some vests simply sacrifice protection for comfort by decreasing the thickness of the ballistics panels. Some vests have open sides to facilitate cooling, but this leaves areas of the core vulnerable.

One common approach is for the officer to wear a sweat-wicking undershirt. The effectiveness of this technique may be marginal at best depending on the permeability of the armor. This technique may keep you dry, but does little to address the heat-retaining issue.

Finally, some solutions provide a means of cooling the vest wearer with a connection to a device causing airflow. For example, U.S. Pat. No. 4,964,282, issued Oct. 23, 1990 and entitled Detachable Bulletproof Vest Air Conditioning Apparatus, provides a hose coupled to the air-conditioning vent of a vehicle. One disadvantage of this solution however, is the requirement that it be connected to a non-portable air source.

BRIEF SUMMARY OF THE INVENTION

The present invention is a personal cooling device for use with body armor, such as bulletproof vests. The present invention comprises a network of tubular members, each tubular member having an inner surface defining a flowpath, an outer surface, and at least two channels extending between the flowpath and the outer surface, wherein said network has an inlet, and wherein the at least two channels of each tubular member have differently-sized volumes, with the channels having the larger volumes being closer to the network inlet than the channels having the smaller volumes; a pump having an inlet and an outlet; and a length of connection tubing in fluid communication with the outlet of the pump and the inlet of the network of tubular members.

DETAILED DESCRIPTION OF EMBODIMENTS OF THE INVENTION

Figure 1:
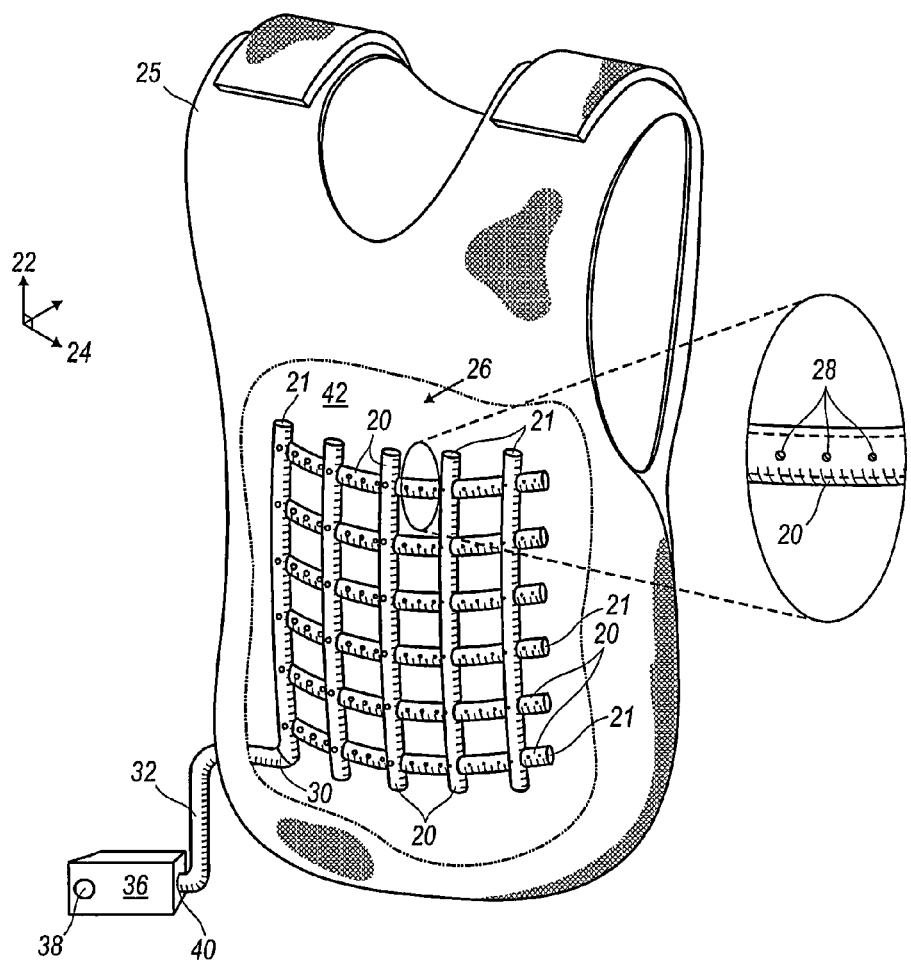
FIG. 1 is a perspective view of one embodiment of the present invention in use with a bulletproof vest, with a portion of the vest cutaway.

FIG. 1 shows one embodiment of the present invention. This embodiment comprises a plurality of hollow tubular members 20 extending in first and second directions 22, 24, with the second direction 24 being perpendicular to the first direction 22, to form a network 26. Each tubular member 20 comprises an inner surface and an outer surface. Each inner surface defines a tubular flowpath through the corresponding tubular member 20. A plurality of channels 28 extends between the inner and outer surfaces. The network 26 has an inlet 30 at one end of a tubular member 20, while the remaining ends of the tubular members 20 are closed. The embodiment further comprises a length of flexible connection tubing 32 connected to the network inlet 30 using the waterproof silicone adhesive (not shown). Use of the adhesive creates an airtight seal between the connection tubing 32 and the network 26. The embodiment further comprises a pump 36 having an inlet 38, and further having an outlet 40 in fluid communication with the connection tubing 32.

The network 26 of tubular members 20 is fastened to the inside surface of a garment 42, with the channels 28 oriented to direct air flow away from the inside surface and, when worn, toward the body of the individual. The pump 36 may then be attached to a belt of the wearer, with the connection tubing 32 running from the pump outlet 40 into the network 26 of tubular members. The wearer may then selectively actuate the pump 36 to cause air received through the pump inlet 38 to move through the outlet 40, through the connection tubing 32 and into the network 26 of tubular members 20. Air flows through the flowpaths of the tubular members 20 and exits the network 26 through the channels 28 toward the wearer, operating to remove heat away from the wearer's body. Body armor, such as a bulletproof vest 25, may then be worn over the embodiment, with the embodiment providing sufficient structural rigidity to space the inner surface of the vest 25 away from the wearer and create a volume for airflow to circulate.

In one alternative embodiment, each channel 28 of a tubular member 20 has a different volume, with the smallest volume channel 28 being positioned furthest from the network inlet 30 and the channel 28 with the largest volume being located closest to the network inlet 30. Generally, air flow through each tubular member 20 tends to move in a straight line until impeded by the closed end, which causes air to be deflected and egress through the channel 28 most proximal to the closed end of the tubular member. By varying the size of the channels as described above, air flow through the channels 28 can be equalized to more evenly distribute the same volume of air through each channel of the tubular member.

In another alternative embodiment, a second network of tubular members is spaced a distance from the first network. For example, a first network of tubular members may be spaced proximal to the abdominal surface or chest, and a second network of tubular channels spaced proximal to the surface of the upper and/or lower back, with the channels oriented to direct airflow toward the wearer of the vest.

Figure 2:
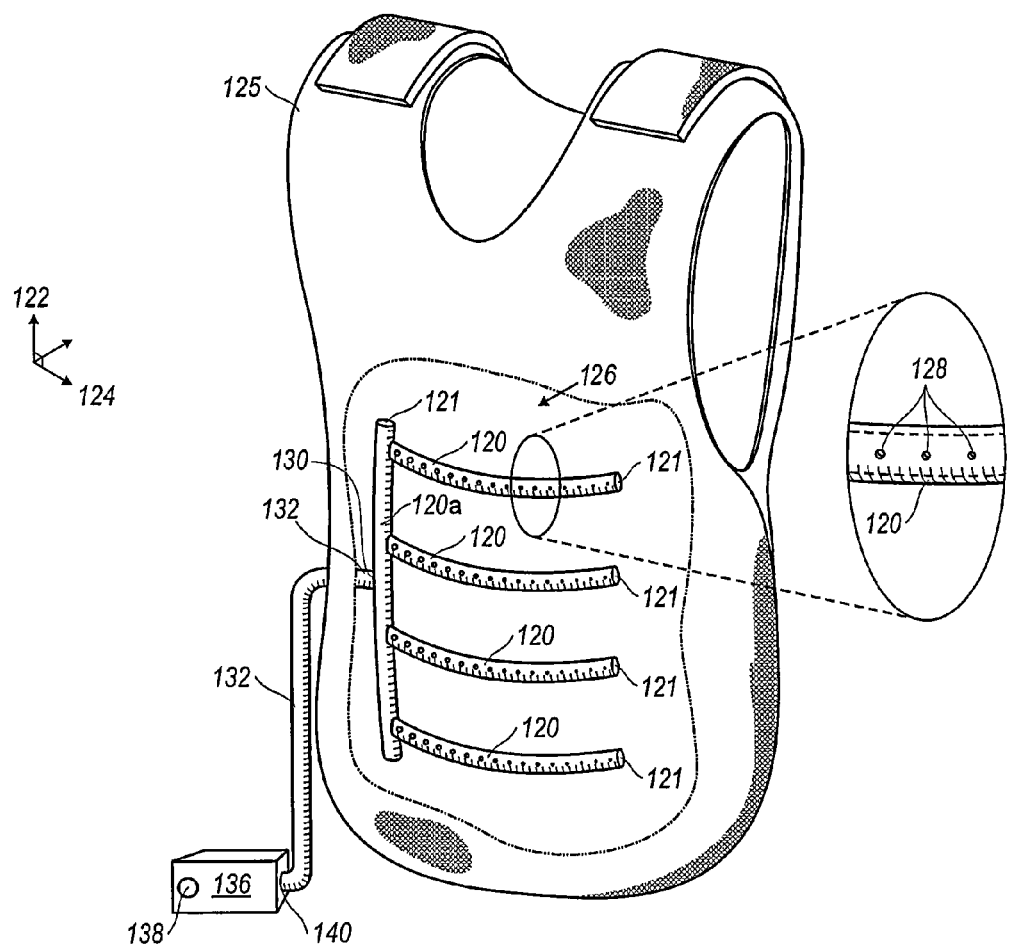
FIG. 2 is a perspective view of a second embodiment of the present invention in use with a bullet proof vest, with a portion of the vest cutaway.

FIG. 2 shows a second embodiment of the present invention. This second embodiment comprises a plurality of hollow tubular members 120 extending in a first direction 122 and a second direction 124 to form a network 126. The network 126 is positioned within the volume defined by body armor, such as a bulletproof vest 125.

Each tubular member 120 comprises an inner surface and an outer surface. Each inner surface defines a tubular flowpath through the corresponding tubular member 120. A plurality of channels 128 extends between the inner and outer surfaces of at least some of the tubular members 120. The network 126 has an inlet 130 at the midpoint of tubular member 120*a*, while the ends 121 of the tubular members 120 are closed. The embodiment further comprises a length of flexible connection tubing 132 adhesively connected to the network inlet 130 using the waterproof silicone adhesive. Use of the adhesive creates an airtight seal between the connection tubing 132 and the network 126. The embodiment further comprises a pump 136 having an inlet 138, and further having an outlet 140 in fluid communication with the connection tubing 132.

Each channel 128 of a tubular member 120 has a different volume, with the smallest volume channel being positioned furthest from the network inlet 130 and the channel 128 with the largest volume within a given tubular member being located closest to the network inlet 130. Generally, air flow through each tubular member 120 tends to move in a straight line until impeded by the closed end 121, which causes air to be deflected and egress through the channel 128 most proximal to the closed end 121 of the tubular member 120. By varying the size of the channels 128 as described above, air flow through the channels 128 can be equalized to more evenly distribute the same volume of air through each channel 128 of each tubular member 120.

The present invention is described in terms of a preferred embodiment in which specific embodiments are described. Those skilled in the art will recognize that alternative embodiments of such system can be used in carrying out the present invention. Other aspects and advantages of the present invention may be obtained from a study of this disclosure and the drawings, along with the appended claims. Moreover, the recited order of the steps of the method described herein is not meant to limit the order in which those steps may be performed.

We claim:

1. A personal cooling device comprising:
   a network of tubular members, each tubular member having an inner surface defining a flowpath, an outer surface, and at least two channels extending between the flowpath and the outer surface, wherein said network has an inlet, wherein the at least two channels of each tubular member have differently-sized volumes, with the channels having the larger volumes being closer to the network inlet than the channels having the smaller volumes;
   a pump having an inlet and an outlet; and
   a length of connection tubing in fluid communication with the outlet of the pump and the inlet of the network of tubular members.

2. The device of claim 1 further comprising a second network of tubular members, each tubular member having an inner surface defining a flowpath, an outer surface, and at least one channel extending between the flowpath and the outer surface, wherein said network has an inlet.

3. The device of claim 1 wherein said pump is a portable pump.

* * * * *